US008993332B2

(12) United States Patent
Tewes et al.

(10) Patent No.: US 8,993,332 B2
(45) Date of Patent: Mar. 31, 2015

(54) METHOD FOR CHARACTERISING THE BIOLOGICAL ACTIVITY OF HELMINTH EGGS, IN PARTICULAR *TRICHURIS* EGGS

(75) Inventors: Bernhard Tewes, Freiburg (DE); Rudolf Wilhelm, Bischweier (DE)

(73) Assignee: Dr. Falk Pharma GmbH, Freiburg (DE)

( * ) Notice: Subject to any disclaimer, the term of this patent is extended or adjusted under 35 U.S.C. 154(b) by 517 days.

(21) Appl. No.: 12/993,517

(22) PCT Filed: May 20, 2009

(86) PCT No.: PCT/EP2009/056106
§ 371 (c)(1),
(2), (4) Date: Dec. 21, 2010

(87) PCT Pub. No.: WO2009/156232
PCT Pub. Date: Dec. 30, 2009

(65) Prior Publication Data
US 2011/0191869 A1  Aug. 4, 2011
US 2012/0060229 A9  Mar. 8, 2012

(30) Foreign Application Priority Data

May 21, 2008 (EP) .................................. 08009344

(51) Int. Cl.
| C12Q 1/68 | (2006.01) |
| G01N 1/28 | (2006.01) |
| G01N 1/30 | (2006.01) |
| G01N 1/44 | (2006.01) |
| G01N 15/10 | (2006.01) |
| G01N 33/00 | (2006.01) |
| G01N 33/48 | (2006.01) |
| G01N 33/50 | (2006.01) |
| C12Q 1/04 | (2006.01) |
| C12Q 1/66 | (2006.01) |

(52) U.S. Cl.
CPC ............... *C12Q 1/6888* (2013.01); *C12Q 1/04* (2013.01); *C12Q 1/66* (2013.01); *G01N 33/5029* (2013.01); *G01N 2333/43526* (2013.01)
USPC .......................................................... 436/63

(58) Field of Classification Search
USPC .......................................................... 436/63
See application file for complete search history.

(56) References Cited

U.S. PATENT DOCUMENTS

| 7,083,911 B2 | 8/2006 | Wood et al. |
| 7,452,663 B2 | 11/2008 | Wood et al. |
| 7,732,128 B2 | 6/2010 | Wood et al. |
| 7,771,923 B2 | 8/2010 | Abromeit |
| 2003/0104507 A1 | 6/2003 | Wood et al. |
| 2005/0048592 A1 | 3/2005 | Wood et al. |
| 2007/0269795 A1 | 11/2007 | Abromeit |
| 2008/0206798 A1 | 8/2008 | Wood et al. |
| 2009/0074818 A1 | 3/2009 | Kapel et al. |

FOREIGN PATENT DOCUMENTS

| WO | WO 02/066671 A2 | 8/2002 |
| WO | WO 2007/076868 A2 | 7/2007 |
| WO | WO 2007/134761 A1 | 11/2007 |

OTHER PUBLICATIONS

Burden et al, Vet. Parasitol. 2(3):307-311, 1976.*
Stevenson, Res. Vet. Sci. 27:193-196, 1979.*
Matthews, J. Helminthol. 59:217-224, 1985.*
Dissanaike et al, Exp. Parasitol. 7:249-253, 1958.*
Bruschi et al, Exp. Parasitol. 75:1-9, 1992.*
de Victorica et al, Water Res. 37:1278-1287, 2003.*
Atkinson et al, Ann. Appl. Biol. 87:167-174, 1977.*
Thitasut, Am. J. Trop. Med. Hyg. 10(1):39-43, 1961.*
Brian M. Pecson, et al., "A Real-Time PCR Method for Quantifying Viable *Ascaris* Eggs Using the First Internally Transcribed Spacer Region of Ribosomal DNA", Applied and Environmental Microbiology, Dec. 2006, vol. 72, No. 12, pp. 7864-7872, XP-002501996.
P. W. Johnson, et al., "An in-vitro test for assessing the viability of *Ascaris suum* eggs exposed to various sewage treatment processes", International Journal for Parasitology, Apr. 1998, vol. 28, No. 4, pp. 627-633, XP008097926.

(Continued)

*Primary Examiner* — Kevin Hill
(74) *Attorney, Agent, or Firm* — Curatolo Sidoti Co., LPA; Joseph G. Curatolo; Salvatore A. Sidoti

(57) ABSTRACT

A method for determining the biological activity of embryonated *Trichuris* eggs is described, in which at least one of the following determinations is carried out:
a) Determination and/or confirmation of the stage of the embryonal development of helminth eggs with the aid of quantitative PCR analysis by using suitable marker sequences for ascertaining the copy number of the genomic DNA,
b) Determination of the metabolic activity of embryonated helminth eggs by means of biochemical and/or molecular biological methods,
c) Determination of the inducibility of gene expression in embryonated helminth eggs,
d) Microscopic determination of the motility of helminth larvae in the egg over long periods of observation after pre-incubation at increased temperatures and/or
e) Determination of the hatching rate of *Trichuris* larvae in a laboratory animal, wherein the intact embryonated eggs recovered from the contents of the intestine are quantified compared to an internal standard.

14 Claims, 8 Drawing Sheets

(56) References Cited

OTHER PUBLICATIONS

J. Boes, et al., "Embryonation and infectivity of *Ascaris suum* eggs isolated from worms expelled by pigs treated with albendazole, pyrantel pamoate, ivermectin or piperazine dihydrochloride", Veterinary Parasitology, Feb. 28, 1998, vol. 75, No. 2-3, pp. 181-190, XP-002449735.

Donald W. Straughan, "Progress in Applying the Three Rs to the Potency Testing of Botulinum Toxin Type A", Alternatives to Laboratory Animals, 2006, vol. 34, No. 3, pp. 305-313.

Helene Kringel. et al., "*Trichuris suis* population dynamics following a primary experimental infection", Veterinary Parasitology, Jun. 30. 2006, vol. 139, No. 1-3, pp. 132-139.

R. J. S. Beer, "Studies on the biology of the life-cycle of *Trichuris suis* Schrank, 1788", Parasitology, Dec. 1, 1973, vol. 67, No. 3, pp. 253-262, XP008113104.

Robert W. Summers, et al., "*Trichuris suis* Therapy for Active Ulcerative Colitis: A Randomized Controlled Trial", Gastroenterology, 2005, vol. 128, pp. 825-832.

Timothy Stinear, "Detection of a Single Viable *Cryptosporidium parvum* in Oocyst Environmental Water Concentrates by Reverse Transcription-PCR", Applied and Environmental Microbiology, Sep. 1, 1996, vol. 62, No. 9, pp. 3385-3390, XP002923031.

International Search Report for PCT/EP2009/056106, Oct. 19, 2009.

Written Opinion of the International Searching Authority for PCT/EP2009/056106, Oct. 19, 2009.

International Preliminary Report on Patentability, Form PCT/IB/373, for PCT International Patent Application No. PCT/EP2009/056106 corresponding to U.S. Appl. No. 12/993,517, mailing date Dec. 16, 2010.

\* cited by examiner

```
T.suis_aa      ------------IGRRYDDAAVQSDMKHWPFKVVSDGGKPKIQVEYKGETKMFTPEBVS  47
C.elegans_aa   RNPBNTVFDAKRLIGRRFDEETVQSDIKHWPFTVKGKQGKFVVEVEVKGEKRBFNAEBIS 120
                           ****;*; ;****;****.*  .. *** :;** ***,! *..**;*

T.suis_aa      AMVLVKMKBTAEAYLG------------------------------------------   63
C.elegans_aa   AMVLQKMKBTAEAVLGHSVRDAVITVPAYFNDSQRQATKDAATIAGLNAIRIINEPTAAA 180
               **** *******.. **
```

CTCCGTCACTGACCACCTTGAAAGGCCAATGCTTCATGTCAGACTG

METHOD FOR CHARACTERISING THE BIOLOGICAL ACTIVITY OF HELMINTH EGGS, IN PARTICULAR TRICHURIS EGGS

CROSS REFERENCE TO RELATED APPLICATIONS

This application is a national stage application of International Application No. PCT/EP2009/056106, filed 20 May 2009, which claims priority from European Patent Application Serial No. 08009344.6, filed 21 May 2008, from which applications priority is claimed, and which are incorporated herein by reference.

The present invention relates to a method for determining the biological activity of helminth eggs, namely of *Trichuris* eggs, preferably *Trichuris suis* eggs, in different stages of their life cycle. The method enables preparations of helminth eggs to be produced, as effective components of therapeutic pharmaceutical products, in a controlled manner and a safe and therapeutically efficient application for humans to be guaranteed.

The influence of parasitic infections on activation of the immune system of their animal hosts is known (Review, D M McKay, Parasitology 2006, 132: 1-12). Such an activation also influences the occurrence and the course of autoimmune diseases. Epidemiological studies show that in regions with high rates of worm infections autoimmune diseases are rarer than in regions in which these infection rates are lower due to better hygienic circumstances. Cytokine profiles of patients with Morbus Crohn, a chronically inflammatory intestinal disease, have shown that Th2 immune cells can be stimulated by helminth infections. Morbus Crohn, a Th1-dominated autoimmune disease, can be prevented or influenced by a helminth infection (Summers et al., Am J Gastroenterol 2003, 98: 2034-2041).

Already in 1971, Beer (Br. Med. J., 1971, 3: 41) reported that *Trichuris suis* could be a suitable nematode for achieving a targeted, moderate infection in a human without inducing the pathogenic effects, which, for example, accompany an infection by the human pathogenic agent *Trichuris trichiura*. According to more recent studies, the infection of humans with *Trichuris suis* only seems to be transient and the worms are evidently repelled before they can multiply. Nevertheless, the positive clinical studies for the use of *Trichuris suis* with chronically inflammatory intestinal diseases point to the fact that this transient infection in humans can trigger a therapeutically effective modulation of the immune system (Summers et al., Am. J. Gastroenterol. 2003, 98: 2034-2041).

The life cycle of *Trichuris suis* begins with depositing the non-embryonated eggs (L0 stage), which are excreted from the infected animal with the faeces. Embryonation to the first larva stage L1 takes place in the ground over a period of 3-6 months. In the first few days after the L1-stage has been reached, larva movements can be observed in the eggs, afterwards the eggs fall into a quiescent state in which they can remain for years without, however, losing their infectivity. After oral ingestion by a suitable host, the L1 larvae hatch out of the egg in the intestinal lumen and within a few hours penetrate into the mucosa of the caecum and colon. The larvae go through further stages of larval development (L2-L4) over the following weeks in the intestinal mucosa until they finally pass out again as adult L5 larvae into the intestinal lumen (Beer, Parasitol. 1973, 67: 253-262).

To pharmaceutically produce *Trichuris suis* eggs (*Trichuris suis* ova=ISO), non-embryonated TSO (L0), which were either deposited in vitro or in situ, are isolated and purified using suitable methods (WO 1999 33479, WO 2007 076868, WO 2007 134761). Subsequently, embryonation takes place under controlled laboratory conditions to form biologically active (L1) TSO, which constitute the pharmaceutically active part of the pharmaceutical product.

Helminth eggs, which are provided for therapeutic applications, can be classified as biological pharmaceutical products. A central parameter, which must be tested in the production and application of biological pharmaceutical products, is the biological activity which is ultimately a measurement for the therapeutic effectiveness of the pharmaceutical product. Without analysing the biological activity, neither the production process can be rationally developed and monitored nor can the dosage of the pharmaceutical product, necessary for the therapeutic effect and safe for the patient, be determined for its planned application in humans. For this reason, only those helminth egg preparations whose biological activity is sufficiently qualified can be safely and effectively used as pharmaceutical products.

Up to now, three analytical methods for *Trichuris suis* have been available, which, however have insufficiently characterised the biological activity.

1. Determination of the embryonation rate (Kringel et al., Vet. Parasitol. 2006, 139: 132-139, Paragraph 2.2 (*Trichuris suis*); also Johnson et al. Intl. J. Parasitol. 1998, 28, 627-633 (Ascaris suum)): The analysis is carried out microscopically. It is evaluated by means of morphological criteria whether the eggs contain an intact, fully formed L1 larva. However, in contrast to the molecular biological method illustrated in this application, it cannot be deduced with absolute certainty from the morphological evaluation alone whether the larvae are, in fact, fully embryonated. A further limitation lies in the fact that the embryonation rate provides no information about the viability and biological activity of the embryonated L1 TSO. In addition, the morphological evaluation requires experience on the part of the observer and the subjective classification of morphological borderline cases limits the correctness and precision of this method.

2. Determination of the infection rate: For *Trichuris suis*, the analysis is carried out in the pig. At a certain point in time after infection, the number of larvae established in the intestinal mucosa is determined and set in relation to the applied dosage of ISO (Kringel et al., Vet. Parasitol., 2006, 139: 132-139, also Summers et al., 2005, Gastroenterology, 128: 825-832 or Johnson et al. Intl. J. Parasitol. 1998, 28, 627-633 (Ascaris suum)). The problem with determining the infection rate is that it is not only dependent on the functionality of the helminth eggs but also equally dependent on individual host factors, such as for example the immune system, the intestinal flora and the intestinal function of the laboratory animals. Determination of the infection rate in laboratory animals is, therefore, intrinsically associated with a high variability and cannot be standardised due to the natural test system, which considerably restricts suitability as a biological activity test. For *Trichuris suis*, the test of infectivity in the pig is associated with a long incubation period of at least three weeks and, due to the high variability, with a high number of animals, which both ethically and economically calls into question the routine use of this test.

Furthermore, Kringel et al. describe the recovery of eggs from the faeces of animals as proof of the biological activity of the helminth eggs, with which the animals were infected. In addition, one has to wait for 7-8 weeks after the animals have been infected until the hatched larvae mature to the L5 stage, mate and deposit eggs themselves. There is no direct, quantitative link from which the infection rate or the biological activity of the adult larvae can be suggested from the number of eggs in the faeces. The method of Kringel et al. clearly has to be differentiated in vivo from the determination of the hatching rate described in this application, since in Kringel et al. the eggs of the next generation are analysed.

3. WO 2007/134761 describes a method for proving the viability of *Trichuris suis* eggs, in which the passage of the eggs through the gastrointestinal passage of a pig is simulated in vitro and the eggs are thereby hatched.

However, the methods described are not sufficient to determine the biological activity of helminth egg preparations with the accuracy required for medicinal products.

Thus, one of the main problems of a biological pharmaceutical product whose biological activity is tested in an animal is, therefore, the standardisation of the preparation. The use of animal models, like the infection of pigs mentioned above, is extremely involved and takes up a considerable amount of time. In the context of the present invention, a method is therefore described in which different types of tests are carried out which relate to different aspects of the development of helminth eggs and their biological activity. At least one of the tests according to the invention has to be carried out with the charge to be analysed in order to reach a reliable conclusion, preferably, however, at least three, more preferably at least four or even five of the presently described tests are carried out, wherein the parameters relevant in each case are determined. The results of the individual tests are considered as a whole, wherein a suitable helminth preparation has to fulfil predetermined limit values in each test, so that it can be concluded from this that the helminth egg preparation is suitable for the pharmaceutical application.

Thus, there is a big demand for a method which can be industrially applied and which comprehensively and reliably analyses the biological activity of TSO and other helminth eggs in different development stages and thereby characterises different biological functions of the helminth eggs. A marketable, medicinal product can only be produced in a controlled manner by means of such a method.

It is an object of the present invention to comprehensively analyse the biological activity of helminth eggs by means of the method elaborated on below and thus, on the one hand, to enable the production process to be tightly controlled and, on the other hand, to enable a safe and therapeutically efficient application in the patient.

Looking at the complex problem and the deficiencies of the methods known to date, it becomes clear that reliably determining biological activity cannot usually be achieved by an individual method step.

The subject matter of the invention is, therefore, a method for determining the biological activity of *Trichuris* eggs which contain fully embryonated larvae and in which at least one of the following determinations is carried out:

Determination of the temperature-induced activity of *Trichuris* eggs using biochemical and/or molecular biological methods, in particular the measurement of ATP content, determination of the inducibility of gene expression in embryonated *Trichuris* eggs, microscopic determination of the motility of *Trichuris* larvae in the egg over long periods of observation after activation by pre-incubation at increased temperatures and/or, determination of the hatching rate of *Trichuris* larvae in a laboratory animal, wherein the intact embryonated eggs recovered from the contents of the intestine are quantified compared to an internal standard.

Therefore, a system consisting of five determinations was developed which in each case analyse different biological functions of the helminths at a specific phase of their life cycle. Although it may be sufficient to apply only one determination method during the individual production steps of a pharmaceutical preparation, as a rule at least 3 of the determinations described in Table 1 below must be carried out to determine the biological activity of the end product.

TABLE 1

| Method step | Exemplary parameters of biological activity |
|---|---|
| 1. Determination of the copy number of genomic DNA | Stage of larval development between L0 and L1 Identity of the organism |
| 2. Determination of the metabolic activity | Viability of the L1 larva in the egg |
| 3. Analysis of the inducible gene expression | Activatability of the dormant L1 larva |
| 4. Determination of the motility index | Ability of the L1 larva to move in the egg (prerequisite for hatching) |
| 5. Determination of the hatching rate in vivo | Hatching rate of the L1 larva from the egg (prerequisite for colonising the host) |

It is preferred if the complete method is carried out with at least three, preferably 4 and more preferably all 5 steps in order to characterise the biological activity of pharmaceutically usable helminth eggs reliably. Where appropriate, it may suffice to carry out just individual steps of the method in order to characterise certain aspects of the biological activity or to monitor sub-steps of production.

The five individual method steps revert back to test principles which have already been described in another connection. The adaptation to embryonated helminth eggs, particularly embryonated eggs of *Trichuris suis*, is new and required the development of a set of new sub-steps which up to now had not yet been described. The entire method, which examines five different aspects of the biological activity and in this way enables a comprehensive characterisation to be made, is also novel and has never been described before for helminth eggs, in particular for eggs of *Trichuris suis*. The preferred common feature for three of the five described methods is the activation of quiescent *Trichuris* larvae by pre-incubation at increased temperature. Another distinctive feature of this method is that it can be carried out with intact, viable helminth eggs and that the measured parameters only depend on the activity of the helminth eggs and not on host factors or on the special abilities of the person carrying out the test, and thus are consequently more objective than the methods applied up to now. Standardisation is hereby possible which is necessary for pharmaceutical use.

By means of the method it is possible to reliably determine the biological activity of helminth egg preparations with the accuracy required for a pharmaceutical product. The precise determination of the biological activity of helminth eggs, as it is described in this invention, is an essential step in the production of an applicable pharmaceutical product.

In the following, the 5 determination methods, which are part of the method, are explained in more detail.

a) Determination of the Copy Number of Genomic DNA

With every cell division during embryonal development, the chromosome set is doubled and is allotted to the two daughter cells. Therefore, the copy number of genomic DNA in the egg can be regarded as the correlation for the number of body cells of the developing larva. Thus, the determination of the copy number of genomic DNA can be used to represent the status of embryonal development of the developing larva at any stage. This is a clear advantage compared to the previously described method (microscopic determination of the embryonation rate, see above), with which only the end result of the embryonation which lasts about 13 weeks can be analysed and which gives no information about whether embryonal development is, in fact, fully completed (i.e. whether the number of cells corresponds to a fully formed L1 larva). The embryonation is a part of the pharmaceutical production process of helminth eggs. A process-accompanying analysis is possible for the first time with the determination of the copy number of genomic DNA. On the one hand, it allows the production process to be developed in a rational way and the effect of process changes to be analysed and, on the other hand, production to be routinely monitored during the embryonation phase With the aid of quantitative PCR technology, the copy number of a particular nucleic acid sequence in a sample can be determined. The more copies that are available in a particular nucleic acid sequence in the sample, the more quickly the amplification plateau will be reached. The number of copies can be determined relatively accurately by means of calibration curves. One of the methods usually used here is the Real Time PCR or also the so-called TaqMan PCR. Alternative nucleic acid amplification methods are known to the man skilled in the art and can also be used to determine the copy number of genomic DNA. The precise copy numbers are generally established with suitable calibration curves.

Preferably, the ITS1-5.8S-ITS2 region, which codes for a part of the ribosomal RNA, is suitable as the preferred marker for the genomic DNA of helminths. For *Trichuris suis* (Cutillas et al., Parasitol Res 2001, 100: 383-389) and for other *Trichuris* types and other helminths, the sequence of the ITS1-5.8S-ITS2 region has already been described. A viability test, in which the embryonal development of Ascaris suum is monitored by means of the quantitative PCR of the IST-1 region, has also already been described (Pecson et al., Appl. Envir. Microbiol., 2006, 72, 7864-7872).

However, this test has another goal, namely the testing of methods for inactivating helminths.

A quantitative PCR (q-PCR), in which a part-sequence from the ITS1-5.8S-ITS2 region is amplified, is particularly suitable for determining the copy number of the marker region and thereby the copy number of the genomic DNA. Since the ITS1 and ITS2 elements are species-specific, the method, besides analysing the stage of the embryonation, is also suitable as a qualitative proof of identity for the organism. A test of this kind is not described in the prior art above all because it was not previously known that the L1 stage of *T. suis* comprises about 1000 cells according to the copy number of the genome (cf. Example 1).

In FIG. 1, the relevant gene sequence of *Trichuris suis*, which can by way of example be used for determining the copy number of genomic DNA, is illustrated. SEQ ID NO:1 shows the relevant gene sequence. The forward primer is expressed as SEQ ID NO:2, the reverse primer as SEQ ID NO:3 and the sequence of the Taqman probe is expressed as SEQ ID NO:4. It is obvious to the person skilled in the art that other parts can also be used from the genome of *Trichuris suis* for determining the copy number. A pre-condition for the sequence is that it must, in this connection, be a nucleotide sequence which specifically occurs in *Trichuris suis* and that there are no similar sequences in other organisms which could possibly find their way into the sample to be analysed as contamination.

Determination of the copy number of genomic DNA also has a secondary effect. It can thereby be confirmed that the desired organism is present in the preparation and in using other suitable sequences it can be demonstrated whether contamination with other organisms exists.

A significant aspect, which must not be overlooked when determining the copy number of genomic DNA, is that helminth eggs have to be disrupted before measurement. As shown in the examples, here a "Potter homogeniser" has proved to be particularly suitable, wherein in a preferred embodiment a volume of 2 ml was used and a gap between 0.01 and 0.03 mm was set. The homogenisation was preferably carried out over a period of 5 to 15 minutes, preferably about 10 minutes. The cell disruption is then always carried out if the cell components have to be available in accessible form for the respective analysis step.

b) Determining the Metabolic Activity

Many methods for determining cell viability are based on analysis of the metabolic activity. Adenosine triphosphate plays a central role in cell metabolism as an energy transmitter and energy store and can be used as a marker for determining intra-cellular metabolic activity. The present invention shows that the detection of this nucleotide can also be used for determining the viability of differentiated organisms, such as L1 larvae of *Trichuris suis*.

The quantitation of adenosine triphosphate in biological systems is made possible by measuring the luminescence with the aid of the luciferase reaction. Luminescence is by definition the emission of "cold" light. Luminescence systems are based on the chemical, biochemical or electrochemical activation of substrates which when returning to their basic state emit a part of the excitation energy in the form of light. When detecting adenosine triphosphate, luciferases are used which were isolated from fireflies (*Photinus pyralis*; firefly). The eukaryotic enzyme catalyses the oxidation of lucerifin to oxyluciferin in the presence of adenosine triphosphate, oxygen and magnesium ions by emitting light. The reaction equation is shown in FIG. 2.

Prerequisites for successfully establishing the determination of adenosine triphosphate in embryonated viable eggs of *Trichuris suis* are the stimulation of an adenosine triphosphate synthesis in the L1 larvae, which is sufficient to measure the luminescence, a full disruption of the eggs by a suitable homogenisation method to release the intra-cellularly formed nucleotide and the quantitative and with that unimpeded detection of adenosine triphosphate from the complex matrix. Surprisingly, and up to now not described, it was found that the ATP content of L1 larvae was low before disruption of embryonal development and is only increased to a constantly high level after suitable activation by incubation over a longer period at a particular temperature. Furthermore, an effective inactivation method is required for distinguishing between living and dead L1 larvae, so that the base value of adenosine triphosphate can be reproducibly determined in organisms which have been killed.

Determining the ATP content for analysing the metabolic activity of helminth egg populations is preferred according to the invention.

To analyse the metabolic activity of individual helminth eggs, staining methods with tetrazolium compounds are also suitable, which were originally developed for freely accessible animal cells in cell cultures or histological slices. The tetrazolium compounds are reduced in metabolically active cells by the effect of mitochondrial enzymes to coloured formazans which are deposited in the cells. In order to transfer the staining methods from freely accessible animal cells to the multi-cellular helminth L1 larvae in the eggs, it is vital that the eggs are pre-treated allowing permeation of the substrate without affecting the viability of the larva in the egg. The L1 larvae of *Trichuris suis* are surrounded by a rigid shell which severely restricts mass transfer with the surrounding area and prevents the permeation of the substances required for the analyses.

Treating the eggs with hypochlorous acid has proved to be advantageous for gently decomposing the egg shell, which has already been described previously (Beer, Parasitol., 1973, 67: 263-278) and which, where appropriate, can be supported by subsequent enzymatic digestion with chitinase and protease.

In order to be able to determine the metabolic activity, a "zero value" must be determined. Here, this is a comparison value from which the respective metabolic activity is determined In a preferred embodiment, the "zero value" is determined with inactive helminth eggs.

Cryoinactivation (quick-freezing and storing at −80° C. over 24 hours) has proved to be a suitable method for inactivating the eggs. The adenosine triphosphate signal from samples inactivated in this way was almost able to be reduced to background noise. The production of cryoinactivated egg samples takes place in phosphate-buffered, physiological sodium chloride solution. The cryoinactivation can, of course, be used with other determination methods.

FIG. 3 shows, by way of example, the effect of the cryoinactivation with the quantitative detection of adenosine triphosphate by means of the luciferase reaction. The effect of pre-incubation can be specifically measured by the use of cryoinactivation. With inactivated (killed) helminth eggs, no increase in adenosine triphosphate can be identified even after pre-incubation. Biologically active helminth eggs, in contrast, have an activity which is obtained by the increase in adenosine triphosphate after pre-treatment at 37° C. over a period of 19 hours.

In one preferred embodiment, 5500 eggs in 550 µl solution are used for each batch. After pre-incubation, the eggs are separated by centrifugation (5 min at 500 rpm) and re-suspended in 225 µl of lysis buffer. To release the cell contents with the adenosine triphosphate formed by incubation, the eggs are homogenised with a Potter homogeniser (volume 2 ml; gap width 0.01-0.03 mm) for 10 min. Only this method results in a full disruption of the eggs and with that a quantitative release of the nucleotide. In order to inactivate adenosine triphosphate splitting hydrolases, the disruption of the eggs is carried out with a lysis buffer (component: phosphoric acid pH 2). From the individual batches, in each case 50 µl are pipetted out onto 96-microwell plates and each batch is diluted with a further 100 µl of phosphate buffer. The luciferase reaction is started by adding 100 µl of commercially available adenosine triphosphate kit. After an incubation of 2 minutes, the microwell plate is read in the luminometer and the luminescence is determined (FIG. 3) The quantitation is carried out against a standard curve of adenosine triphosphate in phosphate buffer (1.0 µM, 0.1 µM, 10 nM, 1 nM, 0.1 nM, 10 pM, 1.0 pM, 0.1 pM). A typical ATP calibration curve is illustrated in FIG. 4.

By targeted adding of adenosine triphosphate to homogenised cryoinactivated samples of embryonated eggs, a recovery of 84% could be achieved within the linear range of the standard curve (1 to 1000 nM). Relevant interaction of the complex matrix of the egg homogenate with the luciferase reaction and the luminescence cannot be recognised thereby.

The example unambiguously shows that the luminescence measurement can be used to distinguish viable, embryonated eggs of *Trichuris suis* from inactivated and thereby unviable eggs. However, the tests can only be successfully carried out with a combination of optimised method parameters consisting of sample activation, sample homogenisation and producing suitable controls by means of an optimised inactivation method. The suitable ATP content of biologically active helminth eggs is in a range of at least 0.01 pmol ATP per egg.

c) Analysis of the Inducible Gene Expression

The principle of this method lies in inducing the gene expression, which can only take place in living cells and by means of which living and dead larvae can be distinguished. In addition, the inducibility of the gene expression is assumedly the prerequisite which enables the dormant L1 larva to pass through different activation states which are necessary to induce the next stages of the life cycle (hatching, establishment in the mucosa, etc.).

The analysis of the expression of heat shock proteins appears to be particularly advantageous, since this can be easily induced by increasing the temperature and the formed messenger RNA (mRNA) is generally stable against rapid decomposition. Within the scope of the present invention, the detection of a gene sequence was successful for the first time in *Trichuris suis*, which is to a large extent homologous to the heat shock protein hsp70 from the helminth *Caenorabhditis elegans*.

In one preferred embodiment of the present invention, the gene expression of the heat shock protein of *T. suis* is analysed. In FIG. 5, the protein sequence of *Trichuris suis* (SEQ ID NO:5), is illustrated compared with the amino acid sequence of the homologous protein from *Caenorabhditis elegans* (SEQ ID NO:6).

The inducible gene expression can take place by determining the content of messenger RNA coding for a specific inducible protein. The nucleotide sequence of the messenger RNA can be derived from the amino acid sequence. It is not a problem for the person skilled in the art to establish suitable forward and reverse primers and inbetween determine the sequence of a Taqman probe. The induction of the gene can then be determined with the aid of a Real Time PCR. A prerequisite for meaningful determination is for a control sample to be measured too which contains killed worm eggs. It must also be a protein which can be easily and reliably induced. One of the examples is the heat shock protein but other genes which can be induced by certain stimuli can also just as well be used for determination.

The detection of the expressed messenger RNA at the individual egg level is also accomplished by fluorescence in situ hybridisation (FISH) with a suitable gene probe. The egg population can then subsequently be particularly advantageously analysed quickly and reliably with the aid of flow cytometry.

The sequence of a suitable probe for in situ hybridisation is illustrated in FIG. 6 (SEQ ID NO:7).

d) Determination of the Motility of Larvae in Intact Helminth Eggs

The principle of the method is based on the detection of body movements as parameters for the functionality of the L1 larva in the egg. The motility of the larva is a prerequisite for it to be able to hatch under suitable environmental conditions. With freely living larvae and worms, such as *C. elegans*, the motility analysis is valid as a reliable proof of viability and function.

Within the scope of the present invention, in the example of *Trichuris suis* it was surprisingly and for the first time found that subtle movements could also be induced in helminth larvae which are not living freely located in the egg by precisely adjusting the environmental temperature. Up to now, it has been described that the larvae fall into a quiescent state after embryonation has been completed and are only activated and hatch after ingestion by a suitable host. The movements of the larvae in the egg are very slow and only detectable if the eggs, as disclosed in the present invention, are examined under a microscope in time lapse over a long period. The microscopic motility test can be automated in combination with image analysis software. The motility index as the parameter for the biological activity of the eggs is calculated as follows:

$$\text{Motility index} = \frac{\text{Number of motile larvae in the observation field}}{\text{Number of analysed eggs in the observation field}}$$

When determining the motility of larvae, precise temperature control is essential for the method to be successful. Firstly, the eggs are pre-incubated over a period of 2 to 30 hours, preferably 4 to 20 hours at a precisely set temperature which is between 36° C. and 42° C., preferably 37° C. to 41° C. and particularly preferably at 39.5° C. After this pre-incubation, the larvae are put under a suitable microscope, wherein the set temperature can be at least approximately maintained. They are then observed using a time-lapse recording over a period of 2 minutes to 4 hours, preferably 30 minutes to 2 hours at a temperature between 36° C. and 42° C., preferably 38° C. to 40° C.

FIG. 7 shows the results of a motility index determined according to the invention, wherein no motility at all can be observed with inactivated worm eggs, and by contrast with active worm eggs the motility index increases with time.

FIG. 8 shows the motility index in connection with different observation periods.

e) Determination of the Hatching Rate in the Intestine

The principle of this method step consists in determining the hatching rate of helminth larvae in the intestine of laboratory animals or alternatively in the contents of the intestine which had been removed from laboratory animals earlier.

The hatching rate in one embodiment can be determined in the contents of the intestine which are removed from laboratory animals and, in fact, preferably at the beginning of the colon or the end of the duodenum. The hatching rate can then be determined in the contents of the intestine without the hatching rate having to be determined directly in a laboratory animal. Furthermore, the method can also be carried out by analysing the eggs which have passed through the intestine and are recovered from the faeces. This has the advantage that the laboratory animal does not have to killed and can be used several times for determining the hatching rate.

In the newly developed method step, the contents of the intestine are analysed relatively shortly after inoculation and the intact eggs, as well as the embryonic membranes left behind after hatching, are counted. A significant advantage compared to the determination of infectivity described in the prior art is that with hatching only the first phase of the life cycle is analysed, which is only slightly affected by individual host factors.

Surprisingly, for *Trichuris suis* it was able to be shown for the first time that the larvae quantitatively hatch not only in the pig, as the suitable host, but also in the rabbit. Hence, for example for *Trichuris suis* a laboratory animal is available with smaller intestinal dimensions, which makes recovering the microscopically small eggs and embryonic membranes considerably easier.

It was surprisingly found that with commercial fluorescent dyes, developed for marking proteins, the egg shell can be permanently stained. Coupling fluorescent dyes with the embryonic membrane makes recovery of the eggs significantly easier, since the contents of the intestine can be analysed by means of fluorescence microscopy.

A further significant technical innovation is the use of non-embryonated or inactivated helminth eggs as the internal fixed standard. These have the same transit or dwell time in the intestine but, in contrast to the embryonated and biologically active eggs, they remain intact when passing through the intestine. By marking the eggs provided as the internal standard with a second (different) fluorescent dye the internal standard and the eggs to be analysed can be easily differentiated.

For analysis, the number of intact eggs marked with fluorescent dye 1 and empty embryonic membranes of the sample to be analysed and the intact eggs of the internal standard marked with fluorescent dye 2 are analysed in the contents of the intestine at a suitable point in time after inoculation. The hatching rate in the intestine can be calculated as follows based on the intact (unhatched) eggs.

Formula for calculating the hatching rate:

$$\text{Hatching-Rate} = 1 - \frac{\frac{[IE]i}{[IS]i}}{\frac{[IE]0}{[IS]0}}$$

with:

– $[IE]$ = Number of intact eggs from the sample to be analysed (marked with dye 1)

– $[IS]$ = Number of intact eggs of the internal standard (marked with dye 2)

– $i$ = Intestinal sample

– $0$ = Inoculation sample

In Table 2 below, the PCR reaction, as well as the preferred determinations and the values which can be obtained thereby, are summarised, which represent preferred limit values of whether the analysed preparation has the required biological activity.

TABLE 2

| Preferred determination | Parameter | Target value |
| --- | --- | --- |
| a) PCR, genomic DNA | Copy number of genomic DNA/egg | Range: 50-1200 copies/egg at d28 (At start of embryonation the copy number is 1 copy/egg; after 28 days embryonation at least one copy number of 50/egg should be achieved) |
| b1) Metabolic activity Variant 1: ATP content | Average ATP content/egg | Range: >1 pmol ATP/embryonated egg |
| b2) Metabolic activity Variant 2: Activity staining | Proportion of eggs with positive activity staining | Range: ≥50% (min. 50% of the eggs should have positive metabolic activity staining) |

TABLE 2-continued

| Preferred determination | Parameter | Target value |
|---|---|---|
| c) Inducible gene expression | Proportion of eggs which show an inducible gene expression | Range: ≥50% (with min. 50% of the eggs the gene expression should be induced) |
| d) Motility index | Proportion of eggs which contain a motile larva | Range: ≥50% (min. 50% of the eggs should contain a motile larva) |
| e) Hatching rate | Proportion of eggs which hatch in the intestine | Range ≥40% (out of min. 40% of the embryonated eggs administered a larva should hatch) |

In a preferred embodiment, the new test method comprises determining the temperature-induced activatability of in vitro embryonated helminth eggs. Two complementary parameters are measured (motility index and average ATP content) which together form the in vitro activity score. The in vitro activity score exhibits a good correlation with the in vivo biological activity. It is, however, only predictive for the biological activity if the larvae used are fully embryonated. A quantitative PCR method is used for this which measures the copy number of the *T. suis* genome in the egg. By means of a novel in vivo hatching test carried out in parallel it is ensured that the checked eggs are, in fact, active under physiological conditions. The preferred method is schematically represented as follows:

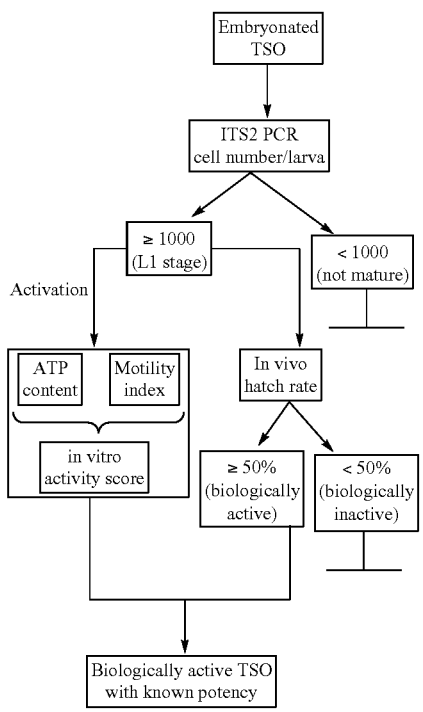

An important aspect of the present invention is determining the temperature-induced activatability in vitro.

L1-TSO after completion of embryonation pass into a quiescent state in which they can survive for years until, after ingestion by the host, they are activated and hatch. Unexpectedly, and up to now not described, it was found that the eggs can also be activated in vitro simply by incubation over a certain period within a certain temperature window without the addition of other factors. The activated state of the eggs is quantified by determining two complementary parameters: the motility of the larvae inside the intact eggs and determination of the ATP content of eggs activated earlier by lysates. Unexpectedly, and contrary to the behaviour described in the literature, the pre-incubation described here induces subtle movements of the larvae in the egg. The movement of the larvae continues for hours without the larvae dying off or hatching out of the egg. Therefore, a preferred embodiment of the method described here is a suitable pre-incubation of the eggs which leads to activation. The proportion of eggs in the population which contain an active, motile larva (motility index) is able to be reliably determined by microscopically observing a sufficiently large number of eggs in time-lapse. However, since this method does not differentiate between different activity states of the individual larvae, thus different levels of the motility/activity, it is combined with the ATP determination which provides a quantitative measure of the total activity of the egg population analysed. Both analysis parameters, the motility index as the direct but discontinuous variable and the ATP content as the indirect but continuous variable, complement one another to reliably determine the in vitro activity, which correlates well with the in vivo activity. An in vitro activity score can be calculated from the two parameters, which correlates well with the in vivo activity of the eggs.

The in vitro method according to the invention clearly differs from the methods known up to now. Determining the embryonation rate, in which eggs are only visually analysed for the presence of fully formed larvae (Kringel et al.), does not, in contrast to the method described here, permit any conclusion to be made about the viability or activity of the larvae. The determination of the hatching rate in vitro by simulating the gastrointestinal passage seems to be considerably more complex and prone to interference in comparison with the method described here. The correlation with the in vivo activity is also not documented for the in vitro hatching test.

In the preferred embodiment of the invention, the state of embryonation is determined. The in vitro activity score only provides meaningful results, which are predictive for the in vivo situation, if the larvae have completely gone through embryonal development. Although larvae which are not fully developed can react positively to the test for temperature-induced activatability, they are not functional and would not be capable of hatching in the host and following the normal life cycle of the larva. With the previously known methods, full embryonal development is microscopically evaluated by means of morphological criteria. This evaluation requires extensive experience, is unreliable and can by nature only be carried out on individual eggs. By contrast, the method according to the invention objectively measures the copy number of the genome in a large egg population, from which the average number of somatic cells per larva can be calculated.

The results of the test for temperature-induced activatability are preferably ensured by a novel in-vivo test which reliably determines the hatching rate in a simple and quick way under physiological conditions. It was surprisingly found that larvae from biologically active eggs quantitatively hatch in the intestinal tract, while previously inactivated eggs survive passage through the intestine unchanged. In the newly developed method, the proportion of active TSO in a preparation is indirectly determined by only the inactive eggs which pass through the intestinal tract of a laboratory animal unchanged being counted. The quantitation is, however, only successful by the use of a newly developed internal standard consisting of fluorescence-marked inactive eggs, which also passes through the intestinal tract unchanged. Surprisingly and unexpectedly, it was additionally found that biologically active TSO also hatch in the intestine of the rabbit. Therefore, an animal model is available as a replacement for the pig, which is more cost-effective and easier to keep and advantageously has a significantly smaller intestinal volume, which makes recovery of the microscopically small eggs easier.

The in vivo test according to the invention can be distanced from the known infectivity test in the pig. The determination of the hatching rate requires only 1-3 days, while the infectivity test lasts several weeks. In addition, when determining the hatching rate only the first step in the life cycle of *T. suis* in the host is analysed, which is scarcely dependent on individual host factors. By contrast, the infection rate in the pig is preferably determined 3-4 weeks after infection and is subject to a natural, biological variability which is primarily explained by the individually differently formed immune system of the host.

A further advantage of the assay described here lies in the fact that the eggs are able to be recovered from the faeces of the animals and the animals do not, for this reason, have to be killed for the test.

BRIEF DESCRIPTION OF DRAWINGS

FIG. 5 shows a comparison of the protein sequence of the putative heat shock protein from *Trichuris suis* (segment) with hsp70 from C.elegans (same bases "*"; bases with similar physicochemical properties "." or ":").

FIG. 6 shows a FISH probe for detecting the expression of heat shock protein mRNA in active embryonated eggs of *Trichuris suis* (T: allyl-amino-thymine bases, to which fluorophores are coupled).

EXAMPLES

Example 1

Based on the ITS2 sequence of *Trichuris suis*, a quantitative PCR method was developed with the aid of the TaqMan system. The target sequence, the primer and the Taqman probe are illustrated below. The target sequence was selected so that it enables *Trichuris suis* to be differentiated from other *Trichuris* types, whose sequence is also known. In this way, the test, in addition to the information about the ITS2 copy number, also provides the qualitative proof that the organism analysed is, in fact, *Trichuris suis*.

In preparation for the sample, the eggs (1000 eggs in 500 µl solution) are homogenised with a Potter homogeniser (volume 2 ml; gap width 0.01-0.03 mm) for 10 min. The microscopic examination proves that surprisingly with this method the embryonic membranes can be broken open, while other disruption methods customary in gene isolation remain unsuccessful with eggs of *Trichuris suis*. After adding 1.54 µg of fish sperm DNA, the egg homogenate is reacted with a commercial kit for isolating genes (DNeasy-Blood and Tissue-Kit; Qiagen) according to the instructions of the manufacturer. With the DNA isolate (total volume 50 µl) a PCR reaction is carried out according to the protocol illustrated in the following table.

TABLE 3

Protocol of the PCR reaction for the target section from the ITS2 region from *T. suis*

Figure 1:
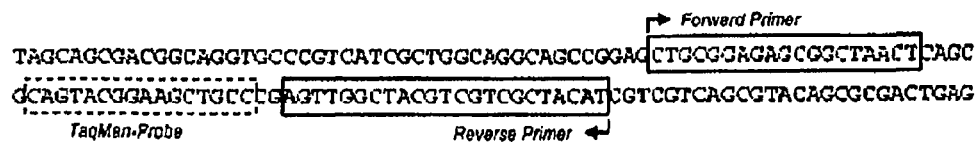
FIG. 1 shows the segment from the ITS2 sequence of Trichuris suis with primers and Taqman probe for the quantitative PCR.
Figure 2:
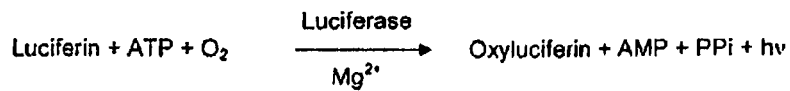
FIG. 2 shows the luciferase reaction equation for quantitative detection of adenosine triphosphate.

| | |
|---|---|
| Instrument: | AB7900HT (Applied Biosystems) |
| Enzymes: | TaqMan Gene Expression Master Mix (Applied Biosystems) |
| Primer, Taqman probe: | See FIG. 1 |
| Final concentration primer: | 900 nM |
| Final concentration Taqman probe: | 200 nM |
| Sample volume: | 5 µl |
| Total volume PCR reaction: | 25 µl |
| Temperature programme: | 50° C./2 min |
| | 95° C./10 min |
| | 40 cycles [95° C./9 sec; |
| | 60° C./1 min] |

The amplification efficiency of the method lies between 92% and 98% and the sensitivity is great enough to be able to determine the copy number of the ITS2 genes in a single egg.

With the PCR method, the ITS2 copy number of non-embryonated and fully embryonated *Trichuris suis* eggs was analysed. The results are illustrated in the following table.

TABLE 4

Quantitative PCR for the ITS2 region in non-embryonated and embryonated eggs of Trichuris suis

| Sample (in each case 1000 eggs) | Ct value | Rel. ITS2 copy number |
|---|---|---|
| Non-embryonated TSO (L0) | 25.5 | 1 |
| Embryonated TSO (L1) | 15.5 | 1024 |

(Ct value (cycle threshold): number of PCR cycles necessary to obtain a fluorescence signal which differs significantly from the background fluorescence)

The PCR analysis shows that the ITS2 copy number in embryonated TSO is higher by approximately a factor of 1000 than the ITS2 copy number in non-embryonated TSO. Since the non-embryonated egg (L0) can be considered as an individual cell, this means that the L1 larva of *T. suis* has ca. 1000 somatic cells. For *T. suis* the number of somatic cells in the L1 larva has not been known up to now. For the related organism *C. elegans* a quantity of 959 somatic cells was found, which tallies well with the ca. 1000 cells found here.

In order to check whether different stages of larval development can be analysed with the test method, TSO were embryonated over 4 weeks and regularly analysed with the ITS2 PCR (Table 5).

TABLE 5

Relative ITS-2 copy number dependent on the duration of the embryonation

| Embryonation duration | Ct (T)-Ct (0) | Rel. ITS2 copy number |
|---|---|---|
| 0 days (L0 state) | 0 | 1 |
| 7 days | 2.52 | 6 |
| 14 days | 6.04 | 66 |
| 21 days | 7.37 | 165 |
| 28 days | 7.76 | 216 |
| 90 days (L1 state) | 10.0 | 1024 |

The example clearly shows that the method can be used to characterise different stages of larval development between L0 and L1 by reference to the number of somatic cells. Therefore, this method is particularly suitable for in-process accompanying analysis of the course of embryonation. Achieving a relative copy number of 50-1200 within the first 28 days of embryonation seems to be a particularly preferred specification when producing a helminth egg preparation.

Example 2

Figure 3:
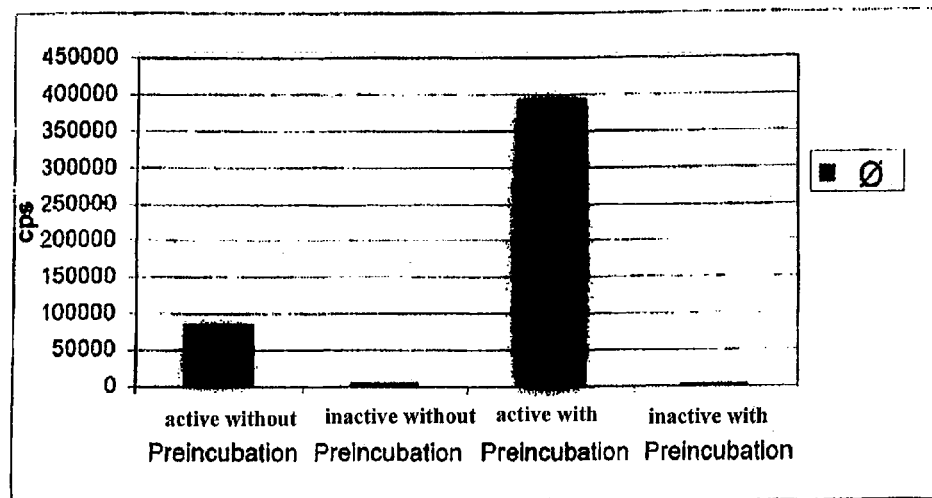
FIG. 3 is a graph showing the effect of the cryoinactivation with the quantitative detection of adenosine triphosphate by means of the luciferase reaction. Explanatory notes for FIG. 3 are as follows:
  Active without pre-incubation: Eggs not inactivated without pre-treatment at 37° C. over 19 hours (eggs in a quiescent state at 2-8° C.).
  Inactive without pre-incubation: Cryoinactivated eggs without pre-treatment at 37° C. over 19 hours.
  Active without pre-incubation: Eggs not inactivated with pre-treatment at 37° C. over 19 hours.
  Inactive without pre-incubation: Cryoinactivated eggs with pre-treatment at 37° C. over 19 hours.
Figure 4:
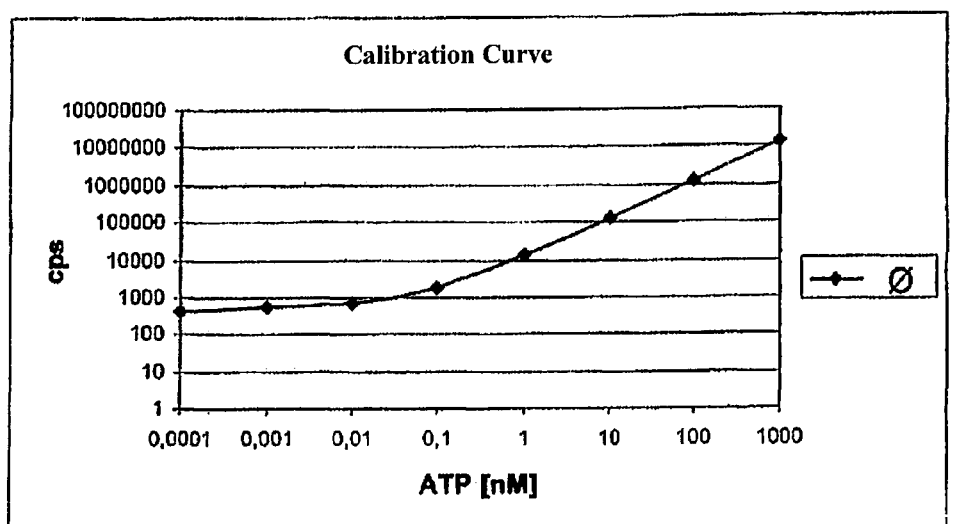
FIG. 4 is a graph showing a standard adenosine triphosphate curve.

For detecting adenosine triphosphate, commercially obtainable kits are available which amongst other things contain the luciferase enzymes required for the reaction as well as the substrate luciferin and magnesium salts. The stimulation of adenosine triphosphate formation by pre-incubation of the embryonated eggs is mandatory. The adenosine triphosphate content of viable embryonated eggs in the quiescent state does not allow a sufficient differentiation from dead eggs to be made (FIG. 3). A method has thereby proved to be suitable, in which the eggs are incubated over a period of 19 hours at 37° C. A significant advantage of the developed analysis method lies in the fact that no sample preparation is necessary for this incubation. The present egg suspensions can be directly used independent of the qualitative and quantitative composition of the medium. Even strongly acidic media with ph values <2 can be used without a sample preparation and have no negative effect on the stimulation of adenosine triphosphate in the eggs. An unambiguous distinction between living and dead F1 larvae is made possible by the incubation (FIG. 3).

Example 3

By means of primers, which were derived from the sequence of the heat shock protein hsp70 found in *Caenorhabditis elegans* and homologous sequences from *Trichuris muris* and *Trichuris vulpis*, a gene sequence was able to be amplified in an RNA isolate from *Trichuris suis*. The new sequence from *Trichuris suis* has, translated into the protein sequence, a 65% match with the protein sequence of the hsp70 protein from *C. elegans* (FIG. 5).

For the putative heat shock protein from *T. suis*, a quantitative RT-PCR method was developed. The quantitation took place in comparison with the constitutively expressed 18S-rRNA. Active embryonated eggs of *T. suis* were subjected to heat shock (20 min at 45° C.) and the expression of the heat shock protein was compared to that in untreated, active *T. suis*.

TABLE 6

Relative Expression of the heat shock protein in active embryonated *T. suis* eggs (L1 larvae) (2 independent experiments with 3 samples in each case; Error: Standard deviation):

| | Experiment #1 | Experiment #2 |
|---|---|---|
| Control | 1.075 ± 0.072 | 1.040 ± 0.029 |
| *T. suis* 45° C., 20 min | 1.690 ± 0.212 | 1.467 ± 0.049 |

The relative expression analysis clearly shows that the expression of the mRNA which is similar to hsp70 can be induced by heat shock (Table 6). Therefore, a gene is available for the activity test whose expression can be actively induced by selecting suitable test conditions.

The detection of the active gene expression on the individual egg is accomplished with the aid of fluorescence in situ hybridisation technology (FISH). In order to be able to detect the putative heat shock protein, the fluorescence-marked DNA probe, for example, illustrated in FIG. 6, was developed (SEQ ID NO:7).

After fluorescence marking the active eggs, the egg population can also be analysed by means of flow cytometry. The advantage, compared to microscopic analysis, lies in the fact that the analysis is carried out more quickly and more objectively.

The example clearly shows that with the method described here the induction of the gene expression in (individual) helminth eggs can be analysed. Hence, for the first time a method is available using which the activatability of dormant L1 helminth larvae can be analysed.

If the induction of the gene expression is used as biological proof of activity during the production of helminth egg preparations, then a suitable acceptance criterion is at 25%-100% of positive eggs, preferably 50-100% of positive helminth eggs.

Example 4

4.1 Dependence of the Motility Index on the Analysis Conditions

Figure 7:
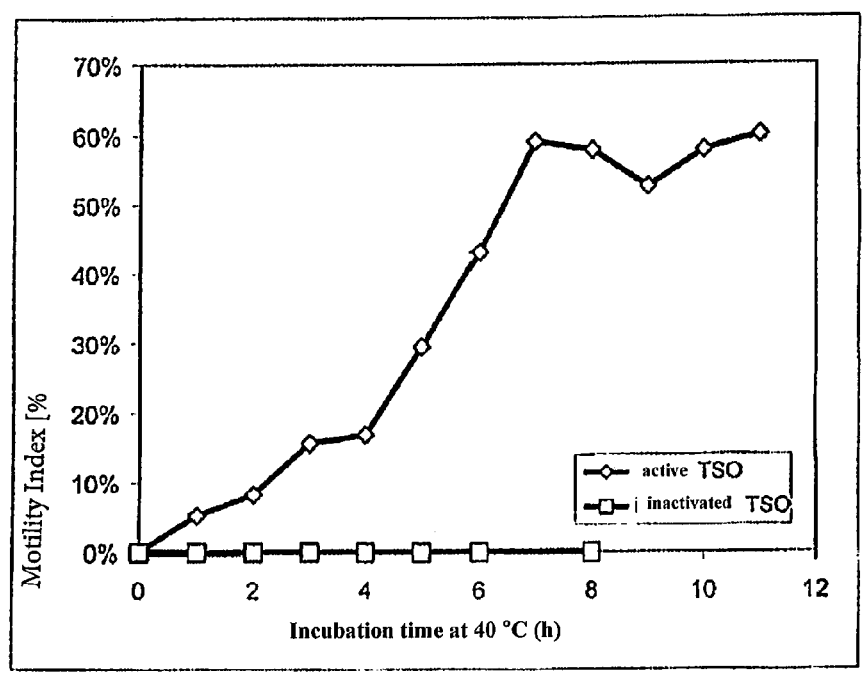
FIG. 7 is a graph showing the results of a motility index of active and thermally inactivated *Trichuris suis* eggs after incubation at 39° C.
Figure 8:
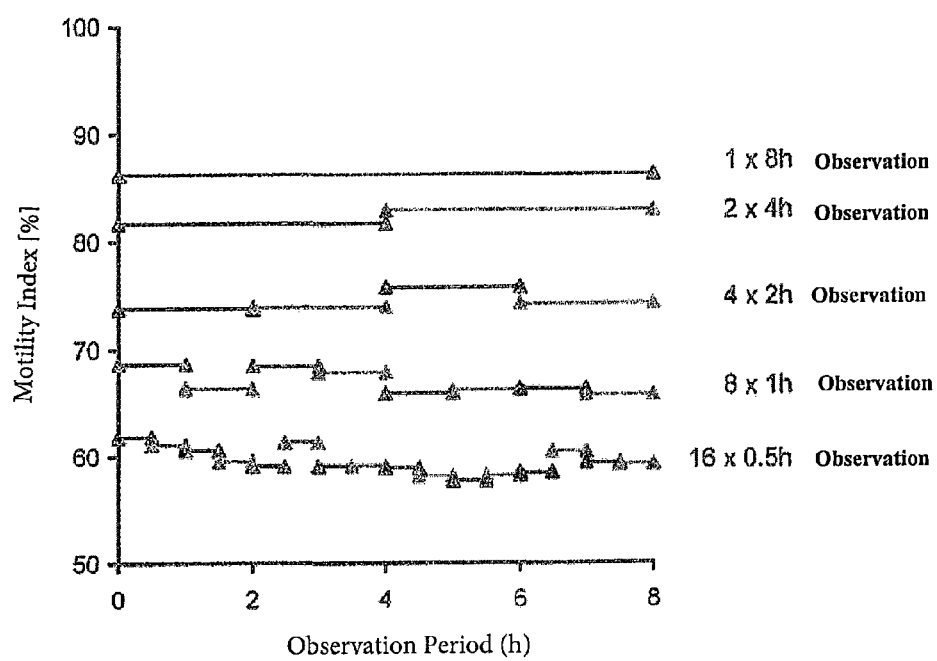
FIG. 8 is a graph showing the motility index of a *Trichuris suis* preparation after different length observation periods at 39.5° C.

Active *Trichuris suis* eggs and *Trichuris suis* eggs inactivated by incubation at 48° C. over 72 hours, were incubated over 11 hours at 39° C. Every hour, the eggs were observed for 5 min in each case and the motility determined. FIG. 7 shows the development of the motility index over time.

The example makes clear that a relatively long pre-incubation at increased temperatures (here: 7 hours at 39° C.) is necessary in order to activate the larvae from the quiescent state and measure a constant, high motility index. This observation was unexpected, since the completely embryonated L1 larvae located in the egg up to now have been classified as immobile (Parasitology 1973, 67: 253-262). Probably, the motility of the larvae in the egg has not been observed before because a long pre-incubation is necessary and the slow movements can only be seen in time-lapse.

The comparison of active and inactivated eggs clearly shows that by analysing the motility biologically active and inactive *Trichuris suis* eggs can be differentiated in a simple way.

Alongside the activation phase, the length of the observation window influences the measured motility index, since the larvae do not move synchronously and consequently a longer observation window increases the probability of detecting sporadic movements in a vital egg. The analysis (FIG. 7) shows this, in which a *Trichuris suis* preparation was observed after an activation phase (8 hours at 37° C.) over periods of varying lengths at 39.5° C. to 40° C. The analysis also shows that the motility remains stable over the entire observation period of 8 hours.

Thus, the activation phase with precise temperature control and the long observation window are characteristic and novel features of this method. Example 4 shows that movements can be induced and measured in dormant L1 larvae, which are still in the egg, by suitable temperature and observation window conditions. Using the method, the motility can be determined in a simple way as a prerequisite for hatching and hence as a parameter for the biological activity of the eggs, and active and inactive L1 larvae can be unambiguously differentiated.

4.2 Advantageous Test Conditions

The following test conditions have proved to be advantageous: A sample with 15,000 helminth eggs in 300 µl of phosphate buffer, pH 7.4 is conveyed into a 96-well plate (base area: 0.31 $cm^2$). At this seeding density, at 200 times magnification ca. 80-150 eggs are situated in the field of view of the microscope. After an 8 hour incubation at 37° C. (activation phase), the temperature is increased to 39.5° C. and 4 observation fields are selected consecutively and observed in each case for 2 hours. A film is thereby recorded with 3 images per minute. The number of eggs and the number of moving larvae are subsequently determined and the motility index is calculated. The motility index of the sample results from the average value of the 4 individual measurements.

4.3 Reproducibility and Precision—Comparison with the Infectivity Test

To analyse the reproducibility of the motility test under the above described conditions, 4 analogous samples of a *Trichuris suis* charge were analysed on 4 different days. The measurement results are listed in the following tables. As a comparison, the results of 4 series of measurements using the infectivity test, which were obtained with the same *Trichuris suis* charge, are listed.

TABLE 7

Determination of the motility index of a *Trichuris suis* charge (Results of 4 independent analyses consisting in each case of 4 measurements)

| | Motility test | | | | Infectivity test | | | | |
|---|---|---|---|---|---|---|---|---|---|
| | | Motility index (%) | | | | | Infectivity rate (%) | | |
| Measurement series | Measurement | Single measurement | Average value | Precision | Measurement series | Lab. animal | Single measurement | Average value | Precision |
| 1 | #1 | 78.4 | 79.1 ± 2.1 | 2.7% | 1 | #1 | 27.4 | 25.9 ± 2.5 | 9.6% |
| | #2 | 77.5 | | | | #2 | 24.7 | | |
| | #3 | 78.2 | | | | #3 | 23.5 | | |
| | #4 | 82.2 | | | | #4 | 29.5 | | |
| | | | | | | #5 | 24.5 | | |
| 2 | #1 | 73.0 | 79.6 ± 5.0 | 6.3% | 2 | #1 | 7.4 | 22.6 ± 13.2 | 58.4% |
| | #2 | 82.4 | | | | #2 | 29.9 | | |
| | #3 | 84.3 | | | | #3 | 26.7 | | |
| | #4 | 78.5 | | | | #4 | 10.7 | | |
| | | | | | | #5 | 38.6 | | |
| 3 | #1 | 87.5 | 82.4 ± 5.1 | 6.2% | 3 | #1 | 17.1 | 32.2 ± 11.8 | 36.6% |
| | #2 | 85.4 | | | | #2 | 33.1 | | |
| | #3 | 80.8 | | | | #3 | 49.9 | | |
| | #4 | 76.0 | | | | #4 | 31.8 | | |
| | | | | | | #5 | 29.1 | | |
| 4 | #1 | 81.1 | 79.8 ± 1.5 | 1.9% | 4 | #1 | 23.4 | 23.8 ± 2.9 | 12.1% |
| | #2 | 80.2 | | | | #2 | 23.7 | | |
| | #3 | 77.6 | | | | #3 | 27.9 | | |
| | #4 | 80.3 | | | | #4 | 24.1 | | |
| | | | | | | #5 | 19.8 | | |

The motility indices from 4 independent measurement series differ from one another by at most 4.2%, by contrast the maximum deviation of the infectivity rate from 4 independent measurement series is 35.5%. The precision of the single measurements in the motility test is between 1.9% and 6.3%, in the infectivity test, by contrast, it is between 9.6% and 58.4%. The motility test is thus far superior to the infectivity test both in terms of reproducibility and in terms of precision.

4.4 Correlation Between Motility and Biological Activity (Correctness)—Comparison with the Infectivity Test To analyse the correlation between motility and biological activity, mixtures consisting of active TSO and thermally inactivated ISO were produced and analysed using the motility test according to the conditions described in 4.2. The thermal inactivation was carried out by heating the eggs at 48° C. over 72 hours. In order to obtain objective counted results, the samples were blinded before measurement.

The relative biological activity was calculated as the quotient from the measured motility index of the sample and the previously determined motility index of the active TSO. The correctness of the measurement results from comparing the relative biological activity and the actual proportion of the active eggs in the sample.

An analagous series of measurements with TSO from the same charge was carried out with the same infectivity test. The laboratory animals were infected with different amounts of active ISO with a known infectivity rate. An admixture of inactivated eggs was dispensed with. The results are illustrated in the following table.

With determinations of lower relative biological activities the precision is below 15%.

The results of the infectivity test deviate by ca. 25-32% from the expected value in the range between 0% and 100% of relative biological activity. The variance of the measured values is between 28% and 80%.

The example clearly shows that the motility index is linearly correlated with the relative biological activity. The motility test is far superior to the infectivity test with regard to correctness and precision.

A suitable range for the motility test as a measurement for the biological activity of helminth egg preparations is 30%-100%, preferably 60-100%.

Example 5

Different mixtures of embryonated, non-embryonated and inactivated, embryonated eggs were, by way of example, orally administered to rabbits. After 8 hours the contents of the intestine of the laboratory animals were analysed microscopically and the intact eggs and the empty embryonic membranes were counted. Since in this assay the eggs were not

TABLE 8

Correctness and precision of the motility test

| | Sample | | | | | |
|---|---|---|---|---|---|---|
| | 1 | 2 | 3 | 4 | 5 | 6 |
| Proportion of active TSO in the sample = expected value of rel. biological activity | 0% | 30.0% | 50% | 70% | 90.0% | 100% |
| Motility index, measurement #1 | 0% | 25.2% | 39.6% | 56.1% | 72.7% | 89.8% |
| Motility index, measurement #2 | 0% | 26.5% | 39.8% | 56.5% | 78.3% | 86.3% |
| Motility index, measurement #3 | 0% | 20.6% | 42.7% | 55.3% | 79.1% | 87.3% |
| Motility index, measurement #4 | 0% | 20.0% | 43.5% | 58.9% | 76.9% | 87.0% |
| Motility index, average value | 0% | 23.1% | 41.4% | 56.7% | 76.8% | 87.6% |
| Motility index, 100% active TSO | 80.2% | 80.2% | 80.2% | 80.2% | 80.2% | 80.2% |
| Rel. biological activity | 0% | 28.8% | 51.6% | 70.7% | 95.7% | 109.2% |
| Correctness (deviation from expected value) | ±0% | −4.1% | +3.3% | +1.0% | +6.4% | +9.2% |
| Precision (variance of measured values) | n.a. | ±14.2% | ±4.8% | ±2.8% | ±3.7% | ±1.7% |

TABLE 9

Correction and precision of the infectivity test

| Sample | 1 | 2 | 3 | 4 |
|---|---|---|---|---|
| Proportion of active TSO in the sample = expected value of rel. biological activity | 0% | 25.0% | 50.0% | 100.0% |
| Infectivity rate, laboratory animal #1 | 0% | 4.1% | 12.4% | 52.2% |
| Infectivity rate, laboratory animal #2 | 0% | 6.2% | 17.2% | 6.3% |
| Infectivity rate, laboratory animal #3 | 0% | 0.4% | 20.4% | 31.1% |
| Infectivity rate, laboratory animal #4 | 0% | 9.5% | 22.6% | 36.0% |
| Infectivity rate, laboratory animal #5 | | 2.3% | 11.8% | 37.9% |
| Infectivity rate, average value | 0% | 4.5% | 16.9% | 32.7% |
| Infectivity rate, 100% active TSO | 26.1% | 26.1% | 26.1% | 26.1% |
| Rel. biological activity | 0% | 17.0% | 64.6% | 125.2% |
| Correctness (deviation from expected value) | ±0% | −31.8% | +29.1% | +25.2% |
| Precision (variance of measured values) | n.a. | ±79.2% | ±28.4% | ±51.1% |

With the motility test illustrated here, the relative biological activity of a TSO sample can be correctly determined with a deviation of <10% from the expected value over the entire range between 0% and 100%. The precision of the measurement (variance of the measured values) is less than 5% in the range between 50% and 100% of relative biological activity.

fluorescence-marked, the hatching rate was calculated according to the ratio of intact embryonated and non-embryonated eggs (using the above formula with [IE]=number of embryonated eggs and [IS]=number of non-embryonated eggs). The following table lists the results of the analysis and the hatching rate calculated from it:

TABLE 10

Number of intact non-embryonated and embryonated *Trichuris suis* eggs and of empty embryonic membranes in the contents of the intestine of rabbits 8 h after the oral administration of mixtures of embryonated, non-embryonated and inactivated eggs.

| Group | Inoculation dose EE | IEE | NEE | Eggs/embryonic membranes in the contents of the intestine EE | NEE | ES | Hatching rate |
|---|---|---|---|---|---|---|---|
| #1 | 36,000 | | 44,000 | 538 | 2050 | 2681 | 67.9% |
| #2 | | 36,000 | 44,000 | 7525 | 8166 | 65 | −12.6% |
| #3 | | | 80,000 | | 3860 | 15 | n.a. |

(EE: intact embryonated eggs; IEE: intact heat-inactivated embryonated eggs; NEE: intact non-embryonated eggs; ES: empty embryonic membranes; n.a.: not applicable)

Comparing the data from Groups 1-3 shows that only active embryonated eggs are able to hatch in the rabbit (recognisable by the distinct decrease in the number of intact embryonated eggs and the presence of a large number of empty embryonic membranes). Inactive embryonated eggs, in contrast, remain unchanged in the intestine (Group 2). This clearly proves that using this method it is possible to differentiate between biologically active and inactivated eggs. Furthermore, non-embryonated eggs also remain intact while passing through the intestine (Group 3). This allows the use of non-embryonated eggs as the internal standard which passes through the intestine of the laboratory animals without being decomposed. This internal standard is necessary because the recovery of the eggs in the contents of the intestine is incomplete and therefore the absolute number of recovered intact eggs is not meaningful. The abovementioned formula is used for calculating the hatching rate taking account of the internal standard. According to this formula, the *Trichuris suis* eggs analysed here show a hatching rate of 67.9%, whereas the inactivated *Trichuris suis* eggs show a hatching rate of 0% (mathematically: −12.6%).

Figure 9:
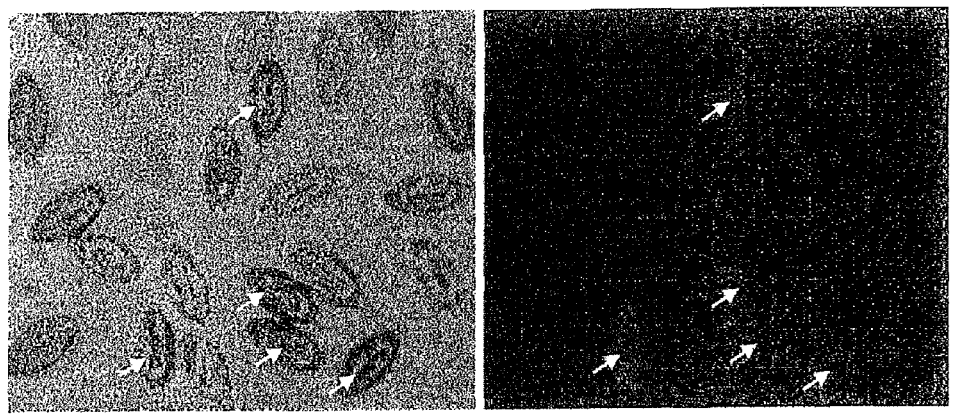
FIG. 9 is a fluorescence microscopic photograph of a mixture consisting of rhodamine-X-marked TSO and unmarked TSO as a control (left: light microscopy; right: fluorescence microscopy). The arrows mark fluorescence-marked TSO.

In order to achieve an improved recovery and a clearer differentiation between the eggs of the sample and the eggs of the internal standard, *Trichuris suis* eggs were covalently marked with a fluorescence-probe. Rhodamine X succinimidyl ester, which according to the manufacturers specification can react with primary amino groups in proteins, was used as the fluorescence-probe by way of example. 20 μl of a 1M sodium bicarbonate solution was added to a suspension of 1000 *Trichuris suis* eggs in 200 μl of phosphate buffer, pH 7.4, and was then reacted with 5 μl of a 0.5% solution of rhodamine X succinimidyl ester in DMSO. The solution was incubated for 1 h at room temperature while being rotated. Then the eggs were purified 8 times in total by centrifugation (10 min at 500 rpm) and exchange of the supernatant buffer. The fluorescence microscopy clearly shows the red colouring of the embryonic membrane (FIG. 9).

The fluorescence marking can be advantageously used for microscopically evaluating the hatching rate. It also enables an objective and quick analysis by means of fluorescence-activated flow cytometry.

Overall, the example clearly shows that by means of the method presented here the hatching phase can be quantitatively analysed and used for determining the biological activity. A suitable range for the hatching rate as a measurement for the biological activity of the helminth-egg-preparations is about 25%-100%.

Example 6

Correlation of the Temperature Induced In Vitro Activatability with the Biological In Vivo Activity 12 TSO samples of varying quality were analysed in order to correlate the temperature-induced activatability with the biological in vivo activity. Firstly, the samples were tested for completeness of embryonic development using the PCR method. Then the motility index and the ATP content were determined following temperature-induced activation. Parallel thereto, an infectivity test was carried out in the pig for each of the 12 samples. The infectivity test was carried out in 5 pigs each according to the method described by Kringel et al. The two in vitro parameters motility and ATP content were summarised in an in vitro activity score:

$$\text{In vitro activity score} = \left(\text{motility index} + \frac{ATP \text{ content}}{50 \text{ nM}}\right) * 0.5$$

TABLE 11

Determination of the activity index of several samples

| Sample | Cell count/larva (ITS2 PCR) | ATP content [nmol] | Motility index [%] | In vitro activity score [%] | Infectivity [%] |
|---|---|---|---|---|---|
| A | >1000 | 6.13 ± 0.8 | 15.30% ± 5.9% | 13.8% ± 3.7% | 7.9% ± 11.5% |
| B | >1000 | 13.40 ± 4.9 | 23.40% ± 4.0% | 25.1% ± 6.9% | 24.3% ± 1.6% |
| C | >1000 | 20.70 ± 2.5 | 51.80% ± 3.2% | 46.6% ± 4.1% | 39.8% ± 3.7% |
| D | >1000 | 36.35 ± 1.8 | 45.10% ± 1.2% | 58.9% ± 2.4% | 43.8% ± 6.7% |
| E | >1000 | 32.75 ± 6.9 | 85.00% ± 2.8% | 75.3% ± 8.3% | 46.8% ± 10.3% |
| F | >1000 | 35.73 ± 3.0 | 88.80% ± 1.1% | 80.1% ± 3.5% | 50.8% ± 11.5% |
| G | >1000 | 41.27 ± 1.6 | 86.90% ± 3.5% | 84.7% ± 3.3% | 67.0% ± 5.0% |
| H | >1000 | 40.20 ± 4.0 | 93.20% ± 1.5% | 86.8% ± 4.8% | 73.4% ± 9.2% |
| I | >1000 | 51.88 ± 4.0 | 76.80% ± 1.2% | 90.3% ± 4.7% | 81.1% ± 4.5% |
| J | >1000 | 46.60 ± 3.5 | 88.60% ± 2.4% | 90.9% ± 4.7% | 80.1% ± 4.4% |
| K | >1000 | 46.44 ± 7.0 | 91.10% ± 1.1% | 92.0% ± 7.6% | 78.8% ± 6.2% |
| L | >1000 | 48.67 ± 3.9 | 91.80% ± 2.3% | 94.6% ± 5.0% | 65.6% ± 17.8% |

Figure 10:
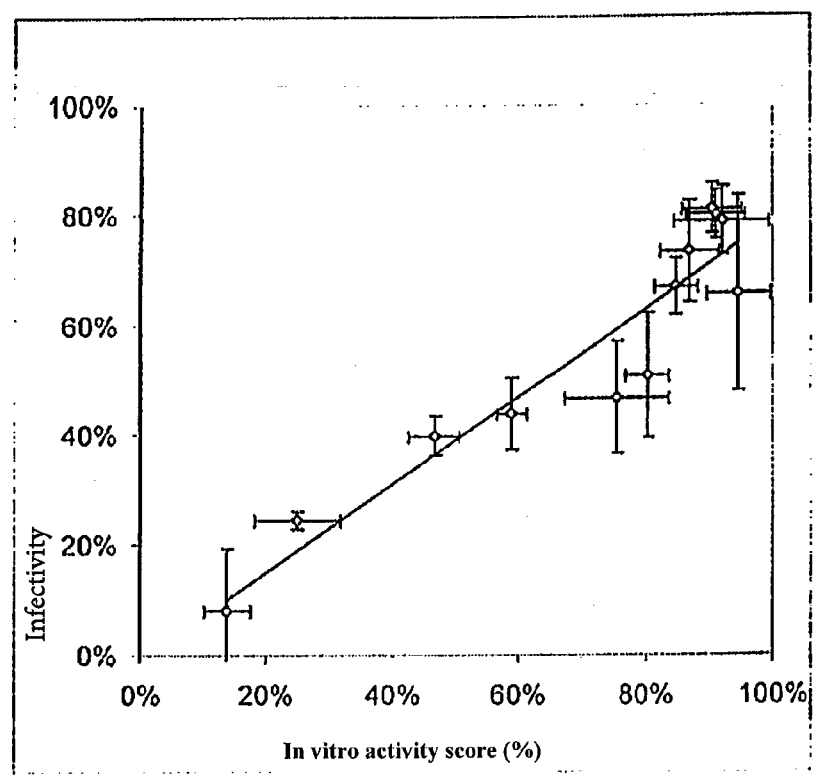
FIG. 10 is a graph showing the correlation between in vitro activity score and infectivity.

The correlation between in vitro activity score and infectivity is shown in FIG. 10.

The example shows a good correlation of the in vitro activity score with the biological in vivo activity. Slight deviations in individual samples are probably rather attributed to weaknesses in the in vivo test which is burdened with an intrinsic unstableness due to the biological variability (host factors).

Measuring a probe using the infectivity test takes 6 weeks, requires the use of 5 pigs and involves considerable labour costs. The in vitro test presented here, consisting of three of the five methods presented, takes 1-2 days and requires comparatively few labour and material costs.

The invention claimed is:

1. A method for determining the biological activity of embryonated *Trichuris* eggs, the method comprising the step of:
   i) determining a hatching rate of *Trichuris* larvae in a laboratory animal, wherein intact embryonated eggs marked with a first probe are recovered from contents of the animal's intestine and are quantified compared to a co-administered internal standard comprising intact non-embryonated or inactive *Trichuris* helminth eggs marked with a second different probe,
   the method further comprising at least two of the following determinations:
   ii) determining and/or confirming a stage of embryonal development of *Trichuris* helminth eggs with the aid of quantitative PCR analysis by using suitable marker sequences for ascertaining a copy number of genomic DNA;
   iii) determining metabolic activity of activated embryonated *Trichuris* helminth eggs by means of biochemical and/or molecular biological methods;
   iv) determining inducibility of gene expression in embryonated *Trichuris* helminth eggs; and/or
   v) determining motility of *Trichuris* helminth larvae in the egg by microscopically observing eggs and calculating a motility index from the number of motile larvae observed in the eggs as compared to the total number of eggs observed, whereby the larvae in the egg are activated after quiescence by pre-incubation at a temperature suitable for activation of quiescent *Trichuris* helminth larvae.

2. The method of claim 1, wherein step (ii) the copy number of the genomic DNA is determined by means of quantitative PCR analysis using specific sequences suitable for *Trichuris* suis.

3. The method of claim 1, wherein step (iii) the ATP content is measured to determine the metabolic activity of embryonated *Trichuris* helminth eggs.

4. The method of claim 3, wherein the *Trichuris* eggs are pre-incubated at a temperature between 36° C. and 42° C. for a period of time between 2 hours and 30 hours in a suspension medium having a pH between 0.1 and 3 before luminescence measurement.

5. The method of claim 1, wherein step (iii), the *Trichuris* eggs are initially treated with a pre-treatment agent selected from hypochlorous acid, chitinase and/or protease, and then stained with tetrazolium salts.

6. The method of claim 1, wherein step (iv), the inducibility of a heat shock protein is determined.

7. The method of claim 1, wherein step (iv), the expression is detected by hybridisation with a fluorescence-marked nucleotide probe.

8. The method of claim 7, wherein the hybridisation is detected with the aid of flow cytometry.

9. The method of claim 1, wherein step (v), the motility of the *Trichuris* helminth larvae in the egg is determined microscopically over periods of 2 minutes to 8 hours with the aid of time-lapse recordings.

10. The method of claim 1, wherein step (i), the *Trichuris* helminth eggs to be examined are marked with first fluorescence probes and the internal standards are marked with second different coloured fluorescence probes.

11. The method of claim 1, wherein step (i), the contents of the intestine of rabbits and/or pigs are used as the test system.

12. The method of claim 1, wherein at least three determinations selected from among the determinations (ii), (iii), (iv) and/or (v) are carried out.

13. The method of claim 1, wherein the *Trichuris* eggs are pre-incubated before carrying out the determination steps of (iii) and/or (v) over a period of at least 30 minutes to 24 hours.

14. The method of claim 13, wherein the pre-incubation contains a change to the temperature.

* * * * *

```
                        SEQUENCE LISTING

<160> NUMBER OF SEQ ID NOS: 7

<210> SEQ ID NO 1
<211> LENGTH: 136
<212> TYPE: DNA
<213> ORGANISM: Trichuris suis

<400> SEQUENCE: 1
tagcagcgac ggcaggtgcc cgtcatcgct ggcaggcagc cggagctgcg gagagcggct      60
aactcagcgc agtacggaag ctgcccgagt tggctacgtc gtcgctacat cgtcgtcagc     120
gtacagcgcg actgag                                                     136

<210> SEQ ID NO 2
<211> LENGTH: 19
<212> TYPE: DNA
<213> ORGANISM: artificial sequence
<220> FEATURE:
<223> OTHER INFORMATION: primer

<400> SEQUENCE: 2
ctgcggagag cggctaact                                                   19

<210> SEQ ID NO 3
<211> LENGTH: 23
<212> TYPE: DNA
<213> ORGANISM: artificial sequence
<220> FEATURE:
<223> OTHER INFORMATION: primer

<400> SEQUENCE: 3
agttggctac gtcgtcgcta cat                                              23

<210> SEQ ID NO 4
<211> LENGTH: 16
<212> TYPE: DNA
<213> ORGANISM: artificial sequence
<220> FEATURE:
<223> OTHER INFORMATION: probe

<400> SEQUENCE: 4
cagtacggaa gctgcc                                                      16

<210> SEQ ID NO 5
<211> LENGTH: 63
<212> TYPE: PRT
<213> ORGANISM: Trichuris suis

<400> SEQUENCE: 5

Ile Gly Arg Arg Tyr Asp Asp Ala Ala Val Gln Ser Asp Met Lys His
1               5                   10                  15

Trp Pro Phe Lys Val Val Ser Asp Gly Gly Lys Pro Lys Ile Gln Val
            20                  25                  30

Glu Tyr Lys Gly Glu Thr Lys Met Phe Thr Pro Glu Glu Val Ser Ala
        35                  40                  45

Met Val Leu Val Lys Met Lys Glu Thr Ala Glu Ala Tyr Leu Gly
    50                  55                  60

<210> SEQ ID NO 6
```

-continued

```
<211> LENGTH: 120
<212> TYPE: PRT
<213> ORGANISM: Caenorhabditis elegans

<400> SEQUENCE: 6

Arg Asn Pro Glu Asn Thr Val Phe Asp Ala Lys Arg Leu Ile Gly Arg
1               5                   10                  15

Arg Phe Asp Glu Glu Thr Val Gln Ser Asp Ile Lys His Trp Pro Phe
                20                  25                  30

Thr Val Lys Gly Lys Gln Gly Lys Pro Val Val Glu Val Glu Val Lys
            35                  40                  45

Gly Glu Lys Arg Glu Phe Asn Ala Glu Glu Ile Ser Ala Met Val Leu
        50                  55                  60

Gln Lys Met Lys Glu Thr Ala Glu Ala Val Leu Gly His Ser Val Arg
65                  70                  75                  80

Asp Ala Val Ile Thr Val Pro Ala Tyr Phe Asn Asp Ser Gln Arg Gln
                85                  90                  95

Ala Thr Lys Asp Ala Ala Thr Ile Ala Gly Leu Asn Ala Ile Arg Ile
            100                 105                 110

Ile Asn Glu Pro Thr Ala Ala Ala
        115                 120

<210> SEQ ID NO 7
<211> LENGTH: 46
<212> TYPE: DNA
<213> ORGANISM: artificial sequence
<220> FEATURE:
<223> OTHER INFORMATION: probe

<400> SEQUENCE: 7
ctccgtcact gaccaccttg aaaggccaat gcttcatgtc agactg              46
```